(12) United States Patent
Wang et al.

(10) Patent No.: US 7,695,449 B2
(45) Date of Patent: Apr. 13, 2010

(54) AUTOMATIC SYRINGE

(76) Inventors: Xinming Wang, c/o Zhongshan Botai Pharmaceutic Instruments Co., Ltd., Room 308, Gaojishu Chanye Chuangye, Zhangxi Kangle Avenue, Torch Development Zone, Zhongshan City, Guangdong Province (CN) 528437; Chunqing Jin, c/o Zhongshan Botai Pharmaceutic Instruments Co., Ltd., Room 308, Gaojishu Chanye Chuangye, Zhangxi Kangle Avenue, Torch Development Zone, Zhongshan City, Guangdong Province (CN) 528437; Yan Liu, c/o Zhongshan Botai Pharmaceutic Instruments Co., Ltd., Room 308, Gaojishu Chanye Chuangye, Zhangxi Kangle Avenue, Torch Development Zone, Zhongshan City, Guangdong Province (CN) 528437

( * ) Notice: Subject to any disclaimer, the term of this patent is extended or adjusted under 35 U.S.C. 154(b) by 0 days.

(21) Appl. No.: 12/096,130

(22) PCT Filed: Oct. 27, 2006

(86) PCT No.: PCT/CN2006/002881
§ 371 (c)(1),
(2), (4) Date: Sep. 23, 2008

(87) PCT Pub. No.: WO2007/065339
PCT Pub. Date: Jun. 14, 2007

(65) Prior Publication Data
US 2009/0105637 A1      Apr. 23, 2009

(30) Foreign Application Priority Data
Dec. 5, 2005   (CN) ................... 2005 1 0096467
Aug. 22, 2006  (CN) ................... 2006 2 0079616 U

(51) Int. Cl.
*A61M 37/00*   (2006.01)
*A61M 39/00*   (2006.01)
*A61M 39/10*   (2006.01)
*A61M 25/16*   (2006.01)
*A61M 25/18*   (2006.01)

(52) U.S. Cl. ................... 604/82; 604/533; 604/89

(58) Field of Classification Search ............. 604/68–72, 604/82, 89–92, 186–187, 533–539, 890.1
See application file for complete search history.

(56) References Cited

U.S. PATENT DOCUMENTS 3,406,684 A * 10/1968 Tsujino .................... 604/70

(Continued)

FOREIGN PATENT DOCUMENTS

CN        2678670 Y        2/2005
WO       2004/110531      12/2004

OTHER PUBLICATIONS

International Search Report issued in PCT/CN2006/002881 mailed on Dec. 28, 2006, with translation, 4 pages.

(Continued)

*Primary Examiner*—Nicholas D Lucchesi
*Assistant Examiner*—Rebecca E Eisenberg
(74) *Attorney, Agent, or Firm*—Osha • Liang LLP

(57) ABSTRACT

A liquid-powder drug prompt-mixing type automatic syringe includes an injecting assembly, a drug-mixing assembly and a shooting device. The injecting assembly includes an injecting outer sleeve, in which the mouth of a blocking ampoule is slidably socketed, a needle is coaxially connected to the blocking ampoule by a hub; the drug-mixing assembly includes a drug-mixing outer sleeve, in which a precharging pressure menstruum bottle by a drug-mixing needle bracket; the shooting device includes a shooting outer sleeve and a spring pushing rod mechanism slidably socketed in the shooting outer sleeve a movable joining mechanism allows the injecting assembly to alternatively connect the drug-mixing assembly and the shooting device respectively. A liquid drug automatic syringe includes said injecting assembly and the shooting device.

15 Claims, 5 Drawing Sheets

U.S. PATENT DOCUMENTS 5,336,180 A * 8/1994 Kriesel et al. .................. 604/82
5,520,639 A * 5/1996 Peterson et al. ................ 604/68
5,807,323 A * 9/1998 Kriesel et al. .................. 604/89
6,746,438 B1 * 6/2004 Arnissolle .................... 604/411
6,902,543 B1 * 6/2005 Cherif-Cheikh et al. ....... 604/82
7,563,245 B2 * 7/2009 Mu ............................. 604/82
2007/0219506 A1 * 9/2007 Andersson .................. 604/207

OTHER PUBLICATIONS

Abstract of CN 2631522Y, published Aug. 11, 2004, supplied by esp@cenet Worldwide database; corresponds to WO2004/110531 above, 1 page.

* cited by examiner

AUTOMATIC SYRINGE

TECHNICAL FIELD

The present invention relates to an automatic syringe for medical use, more particularly, to an instant drug mixing type automatic syringe pre-charged with powder drug and the menstruum and an automatic syringe pre-charged with liquid drug.

BACKGROUND ART

In recent years, the applicant of the present invention has made significant improvements to the constructions of conventional syringes in view of the deficiencies found in the injection operation procedure using conventional syringes and has filed several patent applications in China and other countries. The subject matters of these patent applications filed by the applicant previously involve this and other improvements to the conventional syringes for medical use. However, most of the syringes disclosed in these patent applications do not have the function of instant automatic injections for emergency circumstances, so they are not practical for the needs of instant injection under circumstances such as battlefield self-rescue or other emergent cases. In addition, no prior art discloses an automatic syringe using powder drugs. Powder drugs which often have better curative effects than liquid drugs are not widely used for automatic injection under emergent self-rescue. Conventional syringes are not suitable for emergent injections outside medical facilities because of the complicated drug mixing and adding operation procedures and the risk of contamination.

Chinese patent application No. 200510096467.1 filed by the applicant on Dec. 5, 2005 entitled "Automatic Syringe for Instant Liquid-Powder Drug Mixing" discloses an automatic syringe for solid powder drugs comprising an injecting assembly, a drug mixing assembly, a shooting device and a joining mechanism in which the injecting assembly including a solute vial containing solid powder drug, the drug mixing assembly including a menstruum bottle containing liquid menstruum, the shooting device including a push rod, a pawl and a spring assembly, and the joining mechanism including a central rotary axle and a axle sleeve. The central rotary axle is fixed to the injecting assembly and the axle sleeve is fixed between the drug mixing assembly and the shooting device. The central rotary axle is inserted into the axle sleeve so that the drug mixing assembly and the shooting device can rotate around the central rotary axle so as to alternatively connect with the drug-mixing assembly to complete the drug mixing operation and the automatic injection operation in turn.

Chinese patent application No. 200620079616.3 filed by the applicant on Aug. 22, 2006 entitled "Rotary Automatic Syringe for Instant Liquid-Powder Drug Mixing" discloses major improvements to the injecting assembly, the drug mixing assembly, the shooting device and the joining mechanism of the above-mentioned automatic syringe disclosed in 200510096467.1. A cutting ring and a protective ring are added to the injecting assembly. A returning spring is added to the drug mixing assembly. The push rod in the shooting device includes a push rod for needing feeding, a push rod for injection and a retractable rod. Accordingly two springs are provided in stead—one for the needle feeding push rod and the other for the injection push rod. And two axle sleeves of the joining mechanism having open ends are provided for the drug mixing assembly and the shooting device respectively. And the central rotary axle and injecting assembly are now connected through the axle sleeve having open end in stead of the fixed connection disclosed in 200510096467.1. The above modifications greatly improve the function and effects of the automatic syringe.

The present invention claims priorities of the above-mentioned two Chinese patent applications.

SUMMARY OF INVENTION

It is an object of the present invention to overcome the disadvantages of the existing syringes for medical use by providing an automatic syringe for instant liquid-powder drug mixing and an automatic syringe for liquid drug having in order to simplify the preparative operations before the injection and to avoid possible contamination of the drugs during the preparation stage so as to be more suitable for use in non-medical facilities.

It is another object of the present invention to provide an automatic syringe for instant liquid-powder drug mixing and an automatic syringe for liquid drug having the function of automatic needle feeding and drug pushing so as to be suitable for fast injection and emergency rescue.

The automatic syringe for instant liquid-powder drug mixing is achieved by the following technical solution: the syringe comprises a injecting assembly, a drug mixing assembly and a shooting device; in which, the injecting assembly includes a tubular injecting outer sleeve, in which a blocking ampoule is slidably socketed; the blocking ampoule contains the powder drug and has an open bottom end; a piston is provided inside the blocking ampoule. A needle having two piercing ends is coaxially connected to the mouth of the blocking ampoule through a hub; the needle is located to the front end of the injecting outer sleeve and the bottom of the blocking ampoule is located to the rear end of the injecting outer sleeve;

the drug-mixing assembly includes an tubular drug-mixing outer sleeve; the front end of the drug-mixing outer sleeve is closed having a hole in the centre; a menstruum bottle pre-charged with pressure is slidably socketed in the drug-mixing outer sleeve; a drug-mixing needle having two piercing ends is coaxially connected with the mouth of the menstruum bottle through a drug-mixing needle bracket; the drug-mixing needle is positioned to the front end of the drug-mixing outer sleeve and the bottom of the menstruum bottle is positioned to the rear end of the drug-mixing outer sleeve;

the shooting device includes a tubular shooting outer sleeve and a spring pushing rod mechanism slidably socketed in the shooting outer sleeve;

the rear end of the injecting assembly is alternatively connected with the front end of the drug-mixing assembly and the front end of the shooting device respectively through a rotary joining mechanism;

when the injecting assembly is coaxially connected to the drug-mixing assembly, the drug-mixing needle aims at the piston provided on the bottom of the injecting assembly;

when the injecting assembly is coaxially connected to the shooting device, the front end of the resilient pushing rod rests against the blocking ampoule and the piston.

The automatic syringe for instant liquid-powder drug mixing is further achieved by the following technical solution:

The inner diameter of the injecting outer sleeve enlarges three times along the axis direction of the injecting outer sleeve from its front end to its rear end so as to form three annular steps on the inner wall of the injecting outer sleeve; in which the first annular step is positioned in the front portion of the inner wall of the injecting outer sleeve. The second annular step and the third annular step are positioned in the middle portion of the inner wall of injecting outer sleeve.

The hub is of ring-shaped, the front end of the hub is a closed end and a hole is formed therein. The rear end of the hub is an open end and is slidaly socketed with the mouth of the block ampoule. The hub is able to move forwardly along with the blocking ampoule until the front end of which is rested against the first annular step inside the injecting outer sleeve. The needle extends through the centre of the hub and is fixedly connected to the hub.

The front end of the hub is provided with a jacket for protecting the needle.

The injecting assembly further includes a cutting ring and a protective ring; in which, the cutting ring is a short tube made of thin steel sheet; the outer diameter of the cutting ring equals to or is slightly smaller than the inner diameter of the portion of the injecting outer sleeve between the second annular step and the third annular step; the length of the cutting ring in axis direction equals to the distance between the second annular step and the third annular step of the injecting outer sleeve; the rear end of the cutting ring gradually becomes thinner to form a annular cutting edge;

the annular-shaped protective ring is composed of two pieces of semicircular-shaped plates; the outer diameter of the protective ring is slightly smaller than the inner diameter of the cutting ring and is also slightly smaller than the inner diameter of the injecting outer sleeve in the portion before the second annular step; the hole in the centre of the protective ring allows the mouth of blocking ampoule to pass through; a tubular protrusion is formed around the hole extending to the front end; 2-16 numbers of connecting ribs are formed on the peripheral of the protective ring distributed in equal distances in radial direction of the protective ring; the total length of the outer diameter of the protective ring plus the lengths of any two opposite connecting ribs is slightly less than the length of the inner diameter of the portion of the injecting outer sleeve from the third annular step to the rear end to the injecting outer sleeve;

the cutting ring is rested against the second annular step inside the injecting outer sleeve; the tubular protrusion of the protective ring is rested against the neck of the blocking ampoule; the rear end of the protective ring is rested against the shoulder of the ampoule; the connecting ribs are forwardly rested against the third annular step in the injecting outer sleeve, and the cutting edge of the cutting ring barely touches the connecting ribs formed on the peripheral of the protective ring.

The opening front end of the injecting outer sleeve is provided with a protective cap.

The drug-mixing assembly further includes a bottle seat, a locking ring, a handle and a returning ring; in which, the front end of the bottle seat tightly receives the bottom of the menstruum bottle and rear end of the bottle seat is tightly connected to the handle;

the locking ring is tightly socketed or screwed on the rear end of the drug-mixing outer sleeve to restrict the position of the menstruum bottle to the inside the drug-mixing outer sleeve; the handle extends through the locking ring;

the menstruum bottle is in the returning ring; the front end and the rear end of the returning ring are rested against the inside of the front end of the drug-mixing outer sleeve and the front end of the bottle seat respectively.

The drug-mixing needle bracket has an annular shape. A hole is provided in the centre of the closed front end of the drug-mixing needle bracket to allow the drug-mixing needle to pass through the drug-mixing needle bracket and to be fixed on the needle bracket. The mouth of the menstruum bottle is slidably socketed in the open rear end of the needle bracket. Claws are provided on the inner wall of the needle bracket to engaged with the rear edge of the mouth of the menstruum bottle.

The spring pushing rod mechanism includes a pushing rod for needle feeding, a pushing rod spring for needle feeding, a positioning ring, a pushing rod for injection, a extendable rod, a shooting cap, a shooting cap spring and a fastening ring; in which, the pushing rod for needle feeding, the positioning ring, the pushing rod for injection and the extendable rod have tubular shapes and are in turn slidably socketed with each other;

the diameter of the rear portion of the pushing rod is enlarged to form a step; a plurality of arrow-shaped pawls are formed on the rear end of the pushing rod to engage with the rear end of the shooting outer sleeve; protrusions for restricting the position are formed on the inner wall of the shooting outer sleeve to engage with the step form on the rear portion of the needle feeding pushing rod;

a positioning ring end face having a diameter larger than that of the positioning ring is formed on the rear end of the position ring; a hole is formed in the centre area of the end face of the positioning ring and two protrusions are formed on the two sides of the positioning ring end face 161 respectively;

a slot is formed in one side of the pushing rod along its axis direction. Arrow-shaped pawls are formed on the rear end of the pushing rod and extend through the centre hole of the positioning ring end face to engage with the rear end of the positioning ring end face;

a resilient buckle protruding outwardly and a protrusion are formed on the middle portion of the extendable rod; an end face of the extendable rod having a diameter larger than the extendable rod is formed on the front end of the extendable rod; the resilient buckle and the protrusion slidably engage with the slot of the pushing rod; the protrusion is rested against the rear end of the slot and the end face of the extendable rod is positioned outside the front end of the pushing rod;

the shooting cap has a double ring structure; the outer ring of the shooting cap has notches formed at the two sides corresponding to the protrusions of the positioning ring end face; the rear portion of the shooting cap has a smaller diameter to form a step and the rear end of the shooting cap is closed; the shooting cap is slidably socketed in the shooting outer sleeve; the positioning ring end face is received in the front end of the outer ring of the shooting cap which is rested against the pawls formed on the rear end of the pushing rod;

the rear end of the shooting outer sleeve is tightly socketed in the fastening ring to restrict the front portion of the shooting cap inside the shooting outer sleeve; the rear portion of the shooting cap extends through the ring hole;

the pushing rod spring for needle feeding is covered on the positioning rig and is positioned between the step formed inside the pushing rod and the positioning ring end face;

the pushing rod spring for injection is covered on the rear portion of the pushing rod and is positioned between the shoulder of the pushing rod on the rear end of the pushing rod and the positioning ring end face.

the shooting cap spring is positioned between the step formed inside the outer ring of the shooting cap and the positioning ring end face;

The movable joining mechanism further includes a centre rotary axle, two axle sleeves for the injecting assembly fixed to one side of the injecting outer sleeve, two axle sleeves for the drug-mixing assembly fixed to one side of the drug-mixing outer sleeve and two axle sleeves for the shooting device fixed to the side of the shooting outer sleeve; axle sleeves have open ends and are socketly connected to the centre rotary axle.

The movable joining mechanism further includes a locating axle fixed to rear end of the injecting outer sleeve opposite to the axle sleeves, a locating slot for the drug-mixing assembly fixed to the corresponding side of the front end of the drug-mixing outer sleeve, and a locating slot for the shooting device fixed to the corresponding side of the front end of the shooting outer sleeve. When the injecting assembly is coaxially connected to the drug-mixing assembly and the shooting device alternatively, the locating axle engages into the locating slot for the drug-mixing assembly and the locating slot for the shooting device alternatively.

The movable joining mechanism further includes two locating axles symmetrically formed on the peripheral of the rear end of the injecting outer sleeve, two locating slots for the drug-mixing assembly symmetrically formed on the peripheral of the front end of the drug-mixing outer sleeve and two locating slots for the shooting device symmetrically formed on the peripheral of the front end of the shooting outer sleeve. The locating axles alternatively engage with the locating slots for the drug-mixing assembly and the locating slots for the shooting device.

The automatic syringe for liquid drug according to the present invention is achieved by the following technical solution:

The syringe comprises a injecting assembly, a drug mixing assembly and a shooting device; in which, the injecting assembly includes a tubular injecting outer sleeve, in which a blocking ampoule is slidably socketed; the blocking ampoule contains the powder drug and has an open bottom end and has a sealing rubber stopper on the mouth of the blocking ampoule; a piston is provided inside the blocking ampoule; a needle having two piercing ends is coaxially connected to the mouth of the blocking ampoule through a hub; the needle is located to the front end of the injecting outer sleeve and the bottom of the blocking ampoule is located to the rear end of the injecting outer sleeve; the shooting device includes a tubular shooting outer sleeve and a spring pushing rod mechanism slidably socketed in the shooting outer sleeve.

The injecting assembly is coaxially connected to the shooting device, the front end of the spring pushing rod mechanism rests against the bottom of the blocking ampoule and the piston.

The automatic syringe for liquid drug according to the present invention is further achieved by the following technical solution:

The inner diameter of the injecting outer sleeve enlarges three times along the axis direction of the injecting outer sleeve from its front end to its rear end so as to form three annular steps on the inner wall of the injecting outer sleeve; in which the first annular step is positioned in the front portion of the inner wall of the injecting outer sleeve; the second annular step and the third annular step are positioned in the middle portion of the inner wall of injecting outer sleeve.

The hub is of ring-shaped, the front end of the hub is a closed end and a hole is formed therein, the rear end of the hub is an open end and is slidaly socketed with the mouth of the block ampoule. The hub is able to move forwardly along with the blocking ampoule until the front end of which is rested against the first annular step inside the injecting outer sleeve. The needle extends through the centre of the hub and is fixedly connected to the hub.

The front end of the hub is provided with a jacket for protecting the needle.

The injecting assembly further includes a cutting ring and a protective ring; in which, the cutting ring is a short tube made of thin steel sheet; the outer diameter of the cutting ring equals to or is slightly smaller than the inner diameter of the portion of the injecting outer sleeve the second annular step and the third annular step; the length of the cutting ring in axis direction equals to the distance between the second annular step and the third annular step of the injecting outer sleeve, the rear end of the cutting ring gradually becomes thinner to form a annular cutting edge;

the annular-shaped protective ring is composed of two pieces of semicircular-shaped plates; the outer diameter of the protective ring is slightly smaller than the inner diameter of the cutting ring and is also slightly smaller than the inner diameter of the injecting outer sleeve in the portion before the second annular step; the hole in the centre of the protective ring allows the mouth of blocking ampoule to pass through; a tubular protrusion is formed around the hole extending to the front end; four connecting ribs are formed on the peripheral of the protective ring distributed in equal distances in radial direction of the protective ring; the total length of the outer diameter of the protective ring plus the lengths of any two opposite connecting ribs is slightly less than the length of the inner diameter of the injecting outer sleeve in the portion from the third annular step to the rear end to the injecting outer sleeve;

the cutting ring is rested against the second annular step inside the injecting outer sleeve, the tubular protrusion of the protective ring is rested against the neck of the blocking ampoule; the rear end of the protective ring is rested against the shoulder of the ampoule; the connecting ribs are forwardly rested against the third annular step in the injecting outer sleeve, and the cutting edge of the cutting ring barely touches the connecting ribs formed on the peripheral of the protective ring.

The opening front end of the injecting outer sleeve is provided with a protective cap.

The spring pushing rod mechanism includes a pushing rod for needle feeding, a pushing rod spring for needle feeding, a positioning ring, a pushing rod for injection, a extendable rod, a shooting cap, a shooting cap spring and a fastening ring; in which, the pushing rod for needle feeding, the positioning ring, the pushing rod for injection and the extendable rod have tubular shapes and are in turn slidably socketed with each other;

the diameter of the rear portion of the pushing rod is enlarged to form a step; a plurality of arrow-shaped pawls are formed on the rear end of the pushing rod to engage with the rear end of the shooting outer sleeve; protrusions for restricting the position are formed on the inner wall of the shooting outer sleeve to engage with the step form on the rear portion of the needle feeding pushing rod;

a positioning ring end face having a diameter larger than that of the positioning ring is formed on the rear end of the position ring; a hole is formed in the centre area of the end face of the positioning ring and two protrusions are formed on the two sides of the positioning ring end face 161 respectively;

a slot is formed in one side of the pushing rod along its axis direction; arrow-shaped pawls are formed on the rear end of the pushing rod and extend through the centre hole of the positioning ring end face to engage with the rear end of the positioning ring end face;

a resilient buckle protruding outwardly and a protrusion are formed on the middle portion of the extendable rod; an end face of the extendable rod having a diameter larger than the extendable rod is formed on the front end of the extendable rod; the resilient buckle and the protrusion slidably engage with the slot of the pushing rod; the protrusion is rested against the rear end of the slot and the end face of the extendable rod is positioned outside the front end of the pushing rod;

a shooting cap has a double ring structure; the outer ring of the shooting cap has notches formed at the two sides corresponding to the protrusions of the positioning ring end face; the rear portion of the shooting cap has a smaller diameter to form a step and the rear end of the shooting cap is closed; the shooting cap is slidably socketed in the shooting outer sleeve; the positioning ring end face is received in the front end of the outer ring of the shooting cap which is rested against the pawls formed on the rear end of the pushing rod;

the rear end of the shooting outer sleeve is tightly socketed in the fastening ring to restrict the front portion of the shooting cap inside the shooting outer sleeve; the rear portion of the shooting cap 13 extends through the ring hole;

the pushing rod spring for needle feeding is covered on the positioning rig and is positioned between the step formed inside the pushing rod and the positioning ring end face;

the pushing rod spring for injection is covered on the rear portion of the pushing rod and is positioned between the shoulder of the pushing rod on the rear end of the pushing rod and the positioning ring end face;

the shooting cap spring is positioned between the step formed inside the outer ring of the shooting cap and the positioning ring end face.

The rear end of the injecting outer sleeve is coaxially screwed to or tightly connected to the front end of the shooting outer sleeve.

The rear end of the injecting outer sleeve is fixedly connected to the front end of the shooting outer sleeve to integrate into a whole part.

Locating axles are symmetrically formed on the peripheral of the rear end of the injecting outer sleeve, and locating slots for the shooting device are symmetrically formed on the peripheral of the front end of the shooting outer sleeve. The locating axles engages into the location slots for the shooting device.

DESCRIPTION OF THE PREFERRED EMBODIMENT

Figure 1:
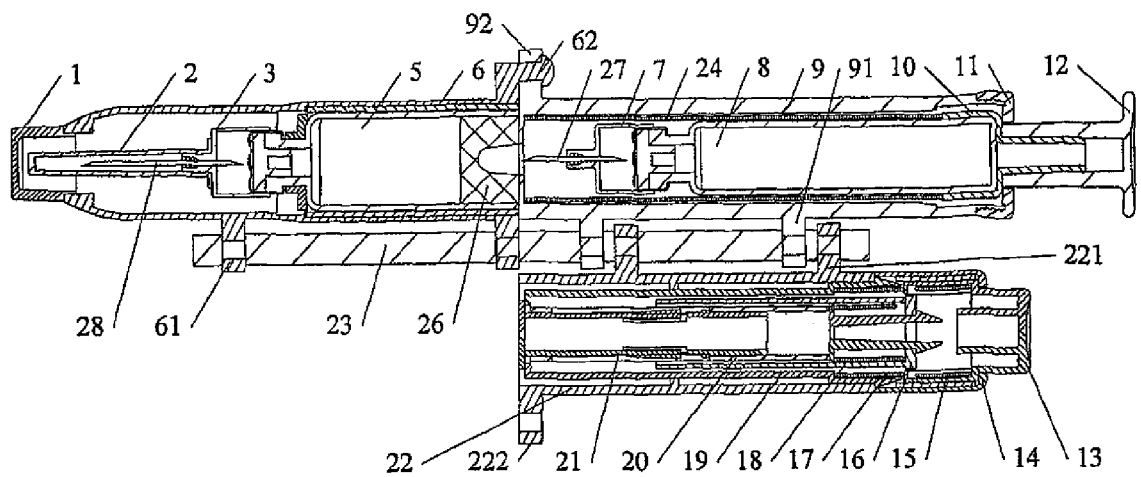
FIG. 1 is a cross-section view showing the initial stage of the first embodiment of the automatic syringe for instant liquid-powder drug mixing.

Hereinafter, the automatic syringe for instant liquid-powder drug mixing and the automatic syringe for liquid drug according to the present invention according to the present invention will be described with reference to accompanying drawings.

1. The first embodiment of the automatic syringe for instant liquid-powder drug mixing according to the present invention-rotary type automatic syringe for instant liquid-powder drug mixing.

Referring to FIG. 1-FIG. 13, the rotary type automatic syringe for instant liquid-powder drug mixing comprises a injecting assembly, a drug mixing assembly and a shooting device; in which, The injecting assembly includes a tubular injecting outer sleeve 6, in which a blocking ampoule 5 is slidably socketed. The blocking ampoule 5 contains the powder drug and has an open bottom end. A piston 26 is provided inside the blocking ampoule 5. A needle 28 having two piercing ends is coaxially connected to the mouth of the blocking ampoule 5 through a hub 3. The needle 28 is located to the front end of the injecting outer sleeve 6 and the bottom of the blocking ampoule 5 is located to the rear end of the injecting outer sleeve 6. The opening front end of the injecting outer sleeve 6 is provided with a protective cap 1.

The inner diameter of the injecting outer sleeve 6 enlarges three times along the axis direction of the injecting outer sleeve 6 from its front end to its rear end so as to form three annular steps on the inner wall of the injecting outer sleeve 6. The first annular step is positioned in the front portion of the inner wall of the injecting outer sleeve 6 to limit the movement of the hub 3 to the front side. The second annular step is positioned in the middle portion of the inner wall of injecting outer sleeve 6 to restrict the position of a cutting ring 25. The distance between the third annular step and the second annular step equals to the width of the cutting ring 25 so as to position a protective ring 4.

The hub 3 is of ring-shaped. The front end of the hub 3 is a closed end and a hole is provided in the centre of the closed front end of the hub 3. The rear end of the hub 3 is an open end and is slidaly socketed with the mouth of the block ampoule 5. The needle 28 extends through the centre of the hub 3 and is fixedly connected to the hub 3. The front end of the hub 3 is provided with a jacket 2 for protecting the needle.

Figure 7:
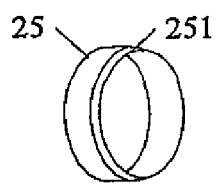
FIG. 7 is a perspective view of the cutting ring according to the embodiments of the present invention.

Referring to FIG. 7, the cutting ring 25 is a short piece of tube made of thin steel sheets. The outer diameter of the cutting ring 25 equals to or is slightly smaller than the inner diameter of the injecting outer sleeve 6 in the portion between the second annular step and the third annular step. The length of the cutting ring 25 in axis direction equals to the distance between the second annular step and the third annular step of the injecting outer sleeve 6. The rear end of the cutting ring 25 gradually becomes thinner to form a annular cutting edge 251.

Figure 8:
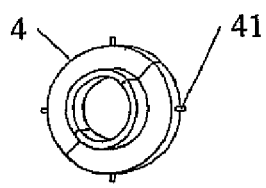
FIG. 8 is a perspective view of the protective ring according to the embodiments of the present invention.

Referring to FIG. 8, an annular-shaped protective ring 4 is composed of two pieces of semicircular-shaped plates. The outer diameter of the protective ring 4 is slightly smaller than the inner diameter of the cutting ring 25 and is also slightly smaller than the inner diameter of the injecting outer sleeve 6 in the portion before the second annular step. The hole in the centre of the protective ring 4 allows the mouth of blocking ampoule 5 to pass through. A tubular protrusion 41 is formed around the hole extending to the front end. Four connecting ribs 42 are formed on the peripheral of the protective ring 4 distributed in equal distances in radial direction of the protective ring 4. The length of the outer diameter of the protective ring 4 plus the lengths of any two opposite connecting ribs 42 is slightly less than the length of the inner diameter of the injecting outer sleeve 6 in the portion from the third annular step to the rear end to the injecting outer sleeve 6.

Figure 9:
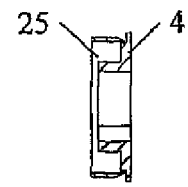
FIG. 9 is a cross-section view in axle direction showing the cutting ring of FIG. 7 joined with the protective ring of FIG. 8.

Referring to FIG. 9, the cutting ring 25 coaxially fits with the protective ring 4. When the cutting ring 25 and the protective ring 4 are mounted in the injecting outer sleeve 6, the end of the cutting ring 25 without the cutting edge is rested against the second annular step inside the injecting outer sleeve 6, the tubular protrusion 41 of the protective ring 4 is rested against the neck of the blocking ampoule 5, the rear end of the protective ring 4 is rested against the shoulder of the ampoule 5, the connecting ribs 42 are forwardly rested against the third annular step in the injecting outer sleeve 6, and the cutting edge 251 of the cutting ring 25 barely touches the connecting ribs 42 formed on the peripheral of the protective ring 4.

The drug-mixing assembly includes an tubular drug-mixing outer sleeve 9. The front end of the drug-mixing outer sleeve 9 is closed having a hole in the centre. A menstruum bottle 8 pre-charged with pressure is slidably socketed in the drug-mixing outer sleeve 9. A drug-mixing needle 27 having two piercing ends is coaxially connected with the mouth of the menstruum bottle 8 through a drug-mixing needle bracket 7. The drug-mixing needle 27 is, positioned to the front end of the drug-mixing outer sleeve 9 and the bottom of the menstruum bottle 8 is positioned to the rear end of the drug-mixing outer sleeve 9.

The drug-mixing needle bracket 7 has an annular shape. A hole is provided in the centre of the closed front end of the drug-mixing needle bracket 7 to allow the drug-mixing needle 27 to pass through the drug-mixing needle bracket 7 and to be fixed on the needle bracket 7. The mouth of the menstruum bottle 8 is slidably socketed in the open rear end of the needle bracket 7. Claws are provided on the inner wall of the needle bracket 7 to hold to the rear edge of the mouth of the menstruum bottle 8.

The drug-mixing assembly further includes a bottle seat 10, a locking ring 11, a handle 12 and a returning ring 24. The front end of the bottle seat 10 tightly receives the bottom of the menstruum bottle 8 and rear end of the bottle seat 10 is tightly connected to the handle 12. The locking ring 11 is tightly socketed or screwed on the rear end of the drug-mixing outer sleeve 9 to restrict the position of the menstruum bottle 8 to the inside the drug-mixing outer sleeve 9. The handle 12 extends through the locking ring 11. The returning ring 24 is put on the menstruum bottle 8. The front end and the rear end of the returning ring 24 are rested against the inside of the front end of the drug-mixing outer sleeve 9 and the front end of the bottle seat 10 respectively.

The shooting device includes a tubular shooting outer sleeve 22 and a spring pushing rod mechanism slidably socketed in the shooting outer sleeve 22.

The spring pushing rod mechanism includes a pushing rod 19 for needle feeding, a pushing rod spring 17 for needle feeding, a positioning ring 16, a pushing rod 20 for injection, a extendable rod 21, a shooting cap 13, a shooting cap spring 15 and a fastening ring 14; in which, The pushing rod 19 for needle feeding, the positioning ring 16, the pushing rod 20 for injection and the extendable rod 21 have tubular shapes and are in turn slidably socketed with each other.

The diameter of the rear portion of the pushing rod 19 is enlarged to form a step. A plurality of arrow-shaped pawls are formed on the rear end of the pushing rod 19 to engage with the rear end of the shooting outer sleeve 22. Protrusions for restricting the position are formed on the inner wall of the shooting outer sleeve 22 to engage with the step form on the rear portion of the needle feeding pushing rod 19.

Figure 12:
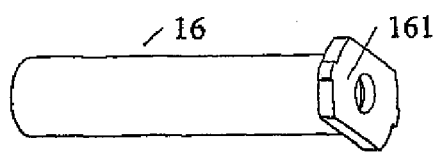
FIG. 12 is a perspective view of the positioning ring according to the embodiments of the present invention.

Referring to FIG. 12, a positioning ring end face 161 having a diameter larger than that of the positioning ring 16 is formed on the rear end of the position ring 16. A hole is formed in the centre area of the end face 161 of the positioning ring 16 and two protrusions are formed on the two sides of the positioning ring end face 161 respectively.

Figure 11:
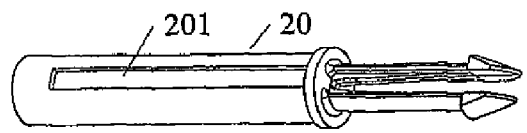
FIG. 11 is a perspective view of the injection pushing rod according to the embodiments of the present invention.

Referring to FIG. 11, a slot 201 is formed in one side of the pushing rod 20 along its axis direction. Arrow-shaped pawls are formed on the rear end of the pushing rod 20 and extend through the centre hole of the positioning ring end face 161 to engage with the rear end of the positioning ring end face 161.

Figure 10:
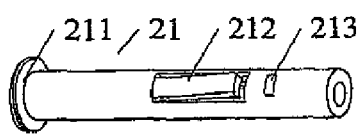
FIG. 10 is a perspective view of the retractable rod of the resilient pushing rod according to the embodiments of the present invention.

Referring to FIG. 10, a resilient buckle 212 protruding outwardly and a protrusion 213 are formed on the middle portion of the extendable rod 21. An end face 211 of the extendable rod 21 having a diameter larger than the extendable rod 21 is formed on the front end of the extendable rod 21. The resilient buckle 212 and the protrusion 213 slidably engage with the slot 201 of the pushing rod 20. The protrusion 213 is rested against the rear end of the slot 201 and the end face 211 of the extendable rod 21 is positioned outside the front end of the pushing rod 19.

Figure 13:
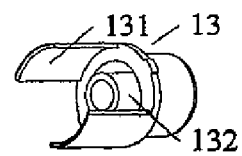
FIG. 13 is a perspective view of the shooting cap according to the embodiments of the present invention.

Referring to FIG. 13, the shooting cap 13 has a double ring structure. The outer ring 131 of the shooting cap 13 has notches formed at the two sides corresponding to the protrusions of the positioning ring end face 161. The rear portion of the shooting cap 13 has a smaller diameter to form a step and the rear end of the shooting cap 13 is closed. The shooting cap 13 is slidably socketed in the shooting outer sleeve 22. The positioning ring end face 161 is received in the front end of the outer ring 131 of the shooting cap 13 which is rested against the pawls formed on the rear end of the pushing rod 19.

The rear end of the shooting outer sleeve 22 is tightly socketed in the fastening ring 14 to restrict the front portion of the shooting cap 13 inside the shooting outer sleeve 22. The rear portion of the shooting cap 13 extends through the ring hole.

The pushing rod spring 17 for needle feeding is covered on the positioning rig 16 and is positioned between the step formed inside the pushing rod 19 and the positioning ring end face 161.

The pushing rod spring 18 for injection is covered on the rear portion of the pushing rod 20 and is positioned between the shoulder of the pushing rod 20 on the rear end of the pushing rod 20 and the positioning ring end face 161.

The shooting cap spring 15 is positioned between the step formed inside the outer ring 131 of the shooting cap 13 and the positioning ring end face 161.

In this embodiment, the rear end of the injecting assembly is alternatively connected with the front end of the drug-mixing assembly and the front end of the shooting device respectively through a rotary joining mechanism.

The rotary joining mechanism includes a centre rotary axle 23, two axle sleeves 61 for the injecting assembly fixed to one side of the injecting outer sleeve 6, two axle sleeves 91 for the drug-mixing assembly fixed to one side of the drug-mixing outer sleeve 9 and two axle sleeves 221 for the shooting device fixed to the side of the shooting outer sleeve 22. Axle sleeves 61, 91 and 221 have open ends and are socketly connected to the centre rotary axle 23.

The rotary joining mechanism further includes a locating axle 62 fixed to rear end of the injecting outer sleeve 6 opposite to the axle sleeves 61, a locating slot 92 for the drug-mixing assembly fixed to the corresponding side of the front end of the drug-mixing outer sleeve 9, and a locating slot 222 for the shooting device fixed to the corresponding side of the front end of the shooting outer sleeve 22. When the injecting assembly is coaxially connected to the drug-mixing assembly and the shooting device alternatively, the locating axle 62 engages into the locating slot 92 for the drug-mixing assembly and the locating slot 222 for the shooting device alternatively.

In this embodiment, FIG. 1 shows the initial state of the rotary type automatic syringe for instant liquid-powder drug mixing prior to use. At this time, the locating axle 62 engages into the locating slot 92 so that the rear end of the injecting assembly is coaxially connected to the front end of the drug-mixing assembly. The hub 3 is partially socketed on the mouth of the blocking ampoule 5. The rear end of the needle 28 does not pierce into the rubber stopper on the mouth of the blocking ampoule 5, and the front end of the needle 28 is inside the front end opening of the injecting outer sleeve 6. The drug-mixing needle bracket 7 is partially socketed on the mouth of the menstruum bottle 8. The rear end of the drug-mixing needle 27 does not pierce into the rubber stopper on the mouth of the menstruum bottle 8, and the front end of the drug-mixing needle 27 aims at the piston 26 on the bottom of the injecting assembly.

Figure 2:
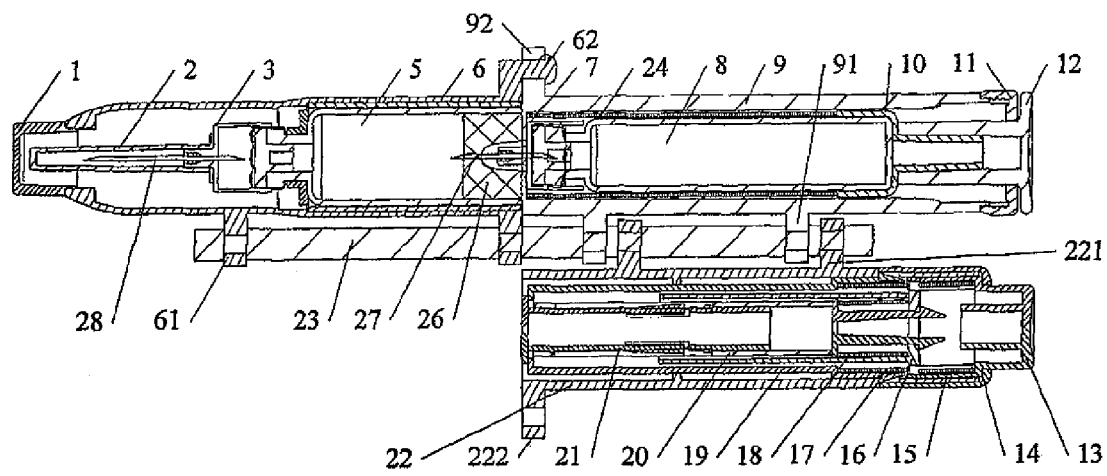
FIG. 2 is a cross-section view showing the drug mixing stage of the first embodiment of the automatic syringe for instant liquid-powder drug mixing.

In the drug mixing operation, point the front end of the syringe downwards and push the handle 12 of the drug-mixing assembly so that the bottle seat 10 will compress the returning spring 24 and push the menstruum bottle 8 to move forward. The drug-mixing needle bracket 7 also moves forward to the front end of the drug-mixing outer sleeve 9. The front end of the drug-mixing needle 27 pierces through the piston 26 on the rear end of the blocking ampoule 5. The mouth of the menstruum bottle 8 completely enters the drug-mixing needle bracket 7. The rear end of the drug-mixing needle 27 pierces through the rubber stopper in the mouth of the menstruum bottle 8 so that the blocking ampoule 5 and the menstruum bottle 8 communicates with each other. The menstruum inside the menstruum bottle 8 enters the blocking ampoule 5 under the force of the pre-charged pressurized gas and mix with the drug powder inside the blocking ampoule 5. At this time the state of the syringe is shown in FIG. 2.

Figure 3:
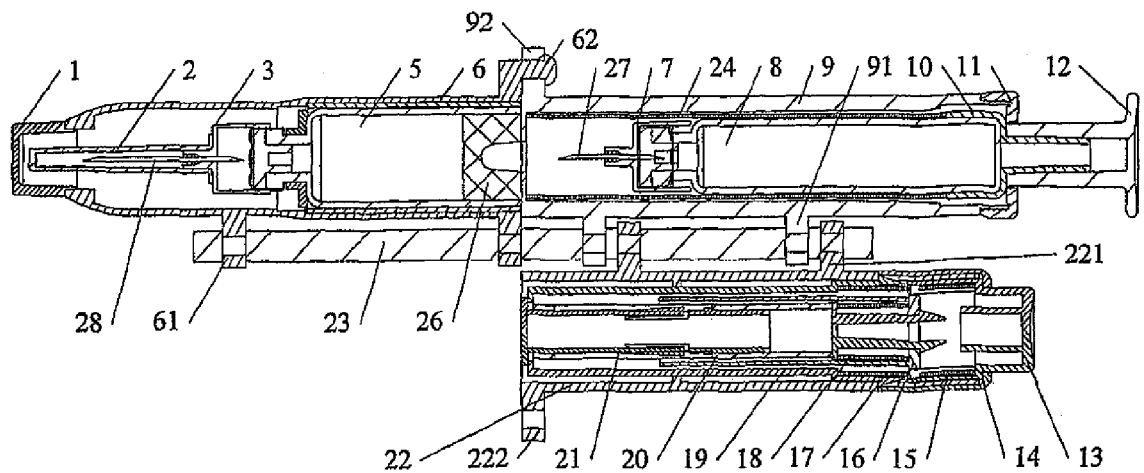
FIG. 3 is a cross-section view showing the first embodiment of the automatic syringe for instant liquid-powder drug mixing after the drug mixing operation is completed.

When the drug mixing operation is completed, release the handle 12 and the bottle seat 10 will move backwards along with menstruum bottle 8 due to the force of the returning spring 24. Because the mouth of the menstruum bottle 8 has completely entered the drug-mixing needle bracket 7, the claws on the inner wall of the drug-mixing needle bracket 7 engages with the back side of the mouth of the menstruum bottle 8. The menstruum bottle 8 moves backwards along with the drug-mixing needle bracket 7. The front end of the drug-mixing needle 27 moves out of the piston 26 and back to the inside of the drug-mixing outer sleeve 9. At this time the state of the syringe is shown in FIG. 3.

Figure 4:
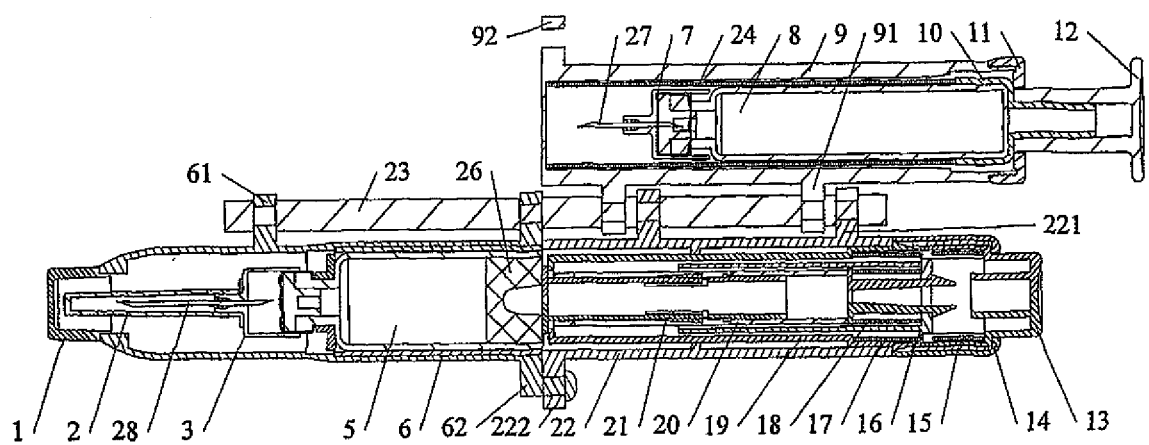
FIG. 4 is a cross-section view showing the injecting assembly joined with the shooting device of the first embodiment of the automatic syringe for instant liquid-powder drug mixing.

Next, rotate the injecting assembly along the centre rotary axle 23 so that the injecting assembly is detached from the drug-mixing assembly. Continue to rotate the injecting assembly until the locating axle 62 engages into the locating slot 222 so that the injecting assembly is coaxially connected with the shooting device and the front end of the spring pushing rod mechanism of the shooting device contacts the bottom of the blocking ampoule 5 and the piston 26. At this time the state of the syringe is shown in FIG. 4

Figure 5:
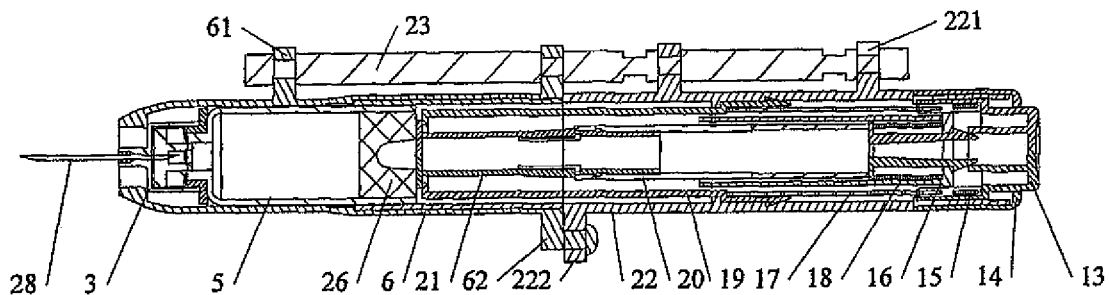
FIG. 5 is a cross-section view showing the needle feeding of first embodiment of the automatic syringe for instant liquid-powder drug mixing.

Because the axle sleeve 91 of the drug-mixing assembly fitting with the centre rotary axle 23 is an open end axle sleeve, so now the drug-mixing assembly can be detached (or, optionally, not detached) from the centre rotary axle 23, then the protective cap 1 and the jacket 2 for the injecting needle on the front end of the injecting assembly are removed thus completing all preparatory operations prior to the injecting operation. Now direct the front end of the syringe to the area to be injected on a human body and press down the shooting cap 13 on the rear end of the shooting outer sleeve 22. Then the front edge of the outer ring 131 of the shooting cap 13 will press the slant face of the arrow-shaped claws on the rear end of the pushing rod 19 for needle feeding so that the claws retracts inwardly and detaches from the rear end of the shooting outer sleeve 22. The pushing rod 19 moves forwardly under the force of the pushing rod spring 17 until the outside of the step on the rear portion of the pushing rod 19 engages with the locating protrusions formed on the inner wall of the shooting outer sleeve 22. At the same time, the extendable rod 21 is brought to move forward and the resilient buckle 212 of the extendable rod 21 is disengaged from the slot 201 formed on one side of the pushing rod 20 and then engages with the front end of the pushing rod 20. The blocking ampoule 5 is moved forward and its shoulder pushes the protective ring 4 to move forward so that the connecting ribs 42 of the protective ring 4 are pressed against the circular cutting edge 251 of the cutting ring 25 and cut off from the protective ring 4. At this time the protective ring 4 is no longer blocked by the third annular step formed on the inner wall of the injecting outer sleeve 6 so that the blocking ampoule 5 along with the protective ring 4 moves abruptly in forward direction inside the injecting outer sleeve 6 and pushes the hub 3 so that the hub 3 also moves forwardly until the front end of the hub 3 rests against the first annular step formed on the inner wall of the injecting outer sleeve 6. At this time the mouth of the blocking ampoule 5 completely enters the hub 3 and the needle 28 pierces into the human body to be injected through the front opening end of the injecting outer sleeve 6. The state of the syringe at this time is shown in FIG. 5.

Figure 6:
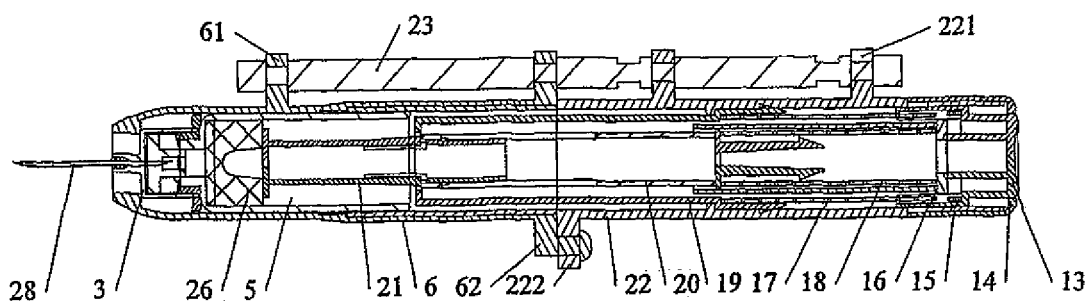
FIG. 6 is a cross-section view showing the first embodiment of the automatic syringe for instant liquid-powder drug mixing when the drug injection operation is completed.

Next, press down the shooting cap 13 and the front edge of the inner ring 132 of the shooting cap 13 in turn presses the slant face of the arrow-shaped claws formed on the rear end of the pushing rod 20 so that the claws retracts inwardly and detaches from the rear end face 161 of the locating ring 16. The pushing rod 20 moves forwardly along with the extendable rod 21 under the force of the pushing rod spring 18 to push the piston 26 to slowly inject the powder drug already mixed with menstruum into the human body until the piston moves to the mouth of the blocking ampoule 5 to inject all mixed drug solution completely into the human body. At this time the state of the syringe is shown in FIG. 6.

2. The second embodiment of the automatic syringe for instant liquid-powder drug mixing according to the present invention—separating type automatic syringe for instant liquid-powder drug mixing—also comprises a injecting assembly, a drug mixing assembly and a shooting device having parts and structures identical to that of the first embodiment. The difference is that this embodiment uses a separately provided joining mechanism for coaxially connecting the rear end of the injecting assembly with the front end of the drug-mixing assembly and the front end of the shooting device alternatively.

The separating joining mechanism includes two locating axles 62 symmetrically formed on the peripheral of the rear end of the injecting outer sleeve 6, two locating slots 92 for the drug-mixing assembly symmetrically formed on the peripheral of the front end of the drug-mixing outer sleeve 9 and two locating slots 222 for the shooting device symmetrically formed on the peripheral of the front end of the shooting outer sleeve 22. The locating axles 62 alternatively engage with the locating slots 92 for the drug-mixing assembly and the locating slots 222 for the shooting device.

Figure 14:
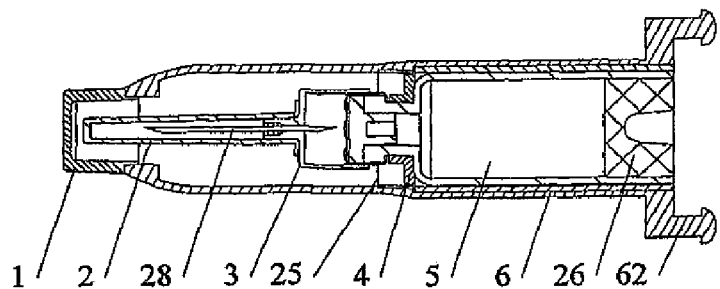
FIG. 14 is a cross-section view of the second embodiment of the injecting assembly of the automatic syringe for instant liquid-powder drug mixing and the embodiment of the automatic syringe for the liquid drug.
Figure 15:
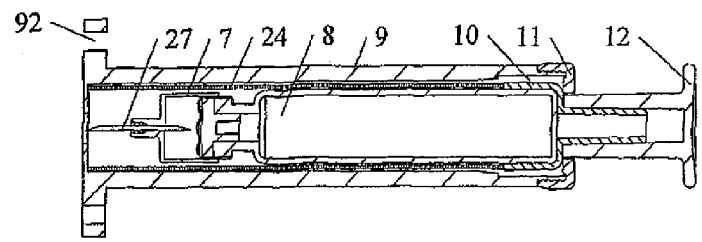
FIG. 15 is a cross-section view of the drug-mixing assembly of the second embodiment of the automatic syringe for instant liquid-powder drug mixing.
Figure 16:
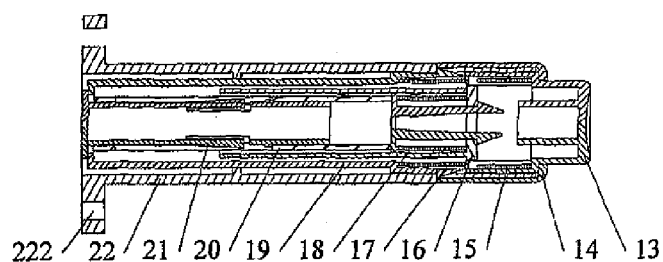
FIG. 16 is a cross-section view of the shooting device of the second embodiment of the automatic syringe for instant liquid-powder drug mixing and the embodiment of the automatic syringe for liquid drug of present invention.
Figure 17:
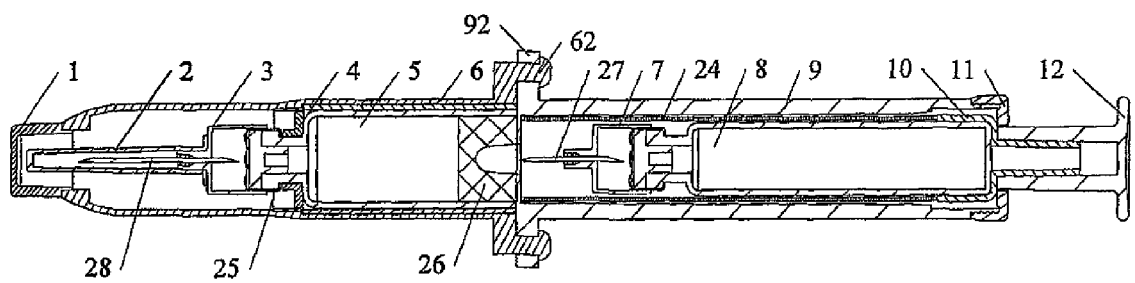
FIG. 17 is a cross-section view of the initial stage of the second embodiment of the automatic syringe for instant liquid-powder drug mixing.

Before use, the injecting assembly, the drug-mixing assembly and the shooting device of the syringe according to the second embodiment are not connected to each other and kept separately, as shown in FIG. 14, FIG. 15 and FIG. 16. When in use, the rear end of the injecting assembly and the front end of the drug-mixing assembly are first coaxially connected, and then the locating axles 62 are engaged into the locating slots 92 by turning the injecting assembly slightly so that the injecting assembly and the drug-mixing assembly are engaged and integrated into one part. At this time the state of syringe is shown in FIG. 17 and new the syringe is ready for drug mixing.

Figure 18:
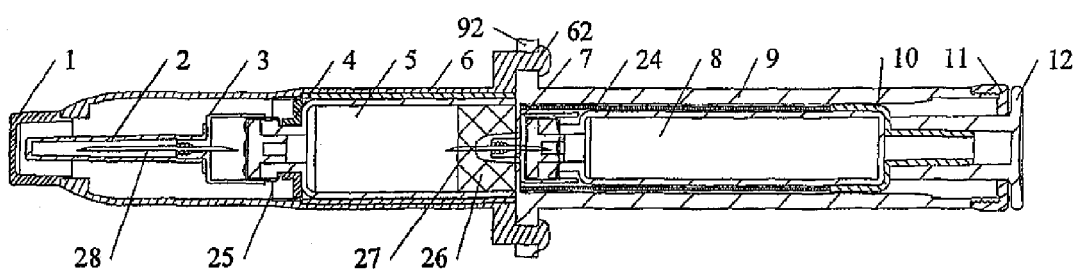
FIG. 18 is a cross-section view of the drug mixing stage of the second embodiment of the automatic syringe for instant liquid-powder drug mixing during the drug mixing stage.
Figure 19:
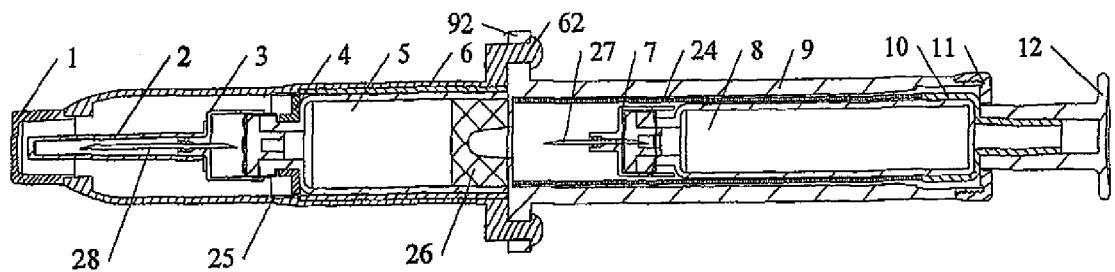
FIG. 19 is a cross-section view of the second embodiment of the automatic syringe for instant liquid-powder drug mixing after the drug mixing operation is completed.

The drug mixing operation in this embodiment is identical to the first embodiment and will not be repeated. FIG. 18 and FIG. 19 show the states of the syringe during the drug mixing operation and after the drug mixing being completed respectively.

Figure 20:
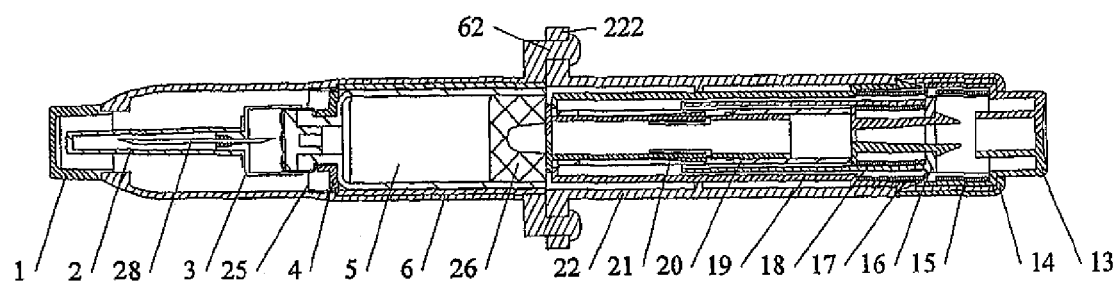
FIG. 20 is a cross-section view of the second embodiment of the automatic syringe for instant liquid-powder drug mixing when the injecting assembly is joined with the shooting device; which is also the initial stage of the embodiment of the automatic syringe for liquid drug.

After the drug mixing operation is completed, detach the injecting assembly from the drug-mixing assembly. Then coaxially connect the rear end of the injecting assembly to the front end of the shooting device. Then engage the locating axles 62 into the locating slots 222 by slightly turning injecting assembly so that the injecting assembly and the shooting device are connected and integrated into one part. At this time the state of syringe is shown in FIG. 20 and the syringe is ready for injection.

Figure 21:
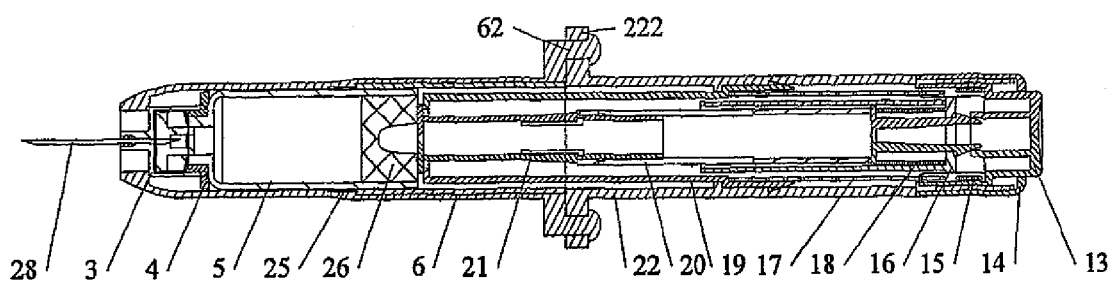
FIG. 21 is a cross-section view of the needle feeding of the second embodiment of the automatic syringe for instant liquid-powder drug mixing and the needle feeding of the embodiment of the automatic syringe for liquid drug.
Figure 22:
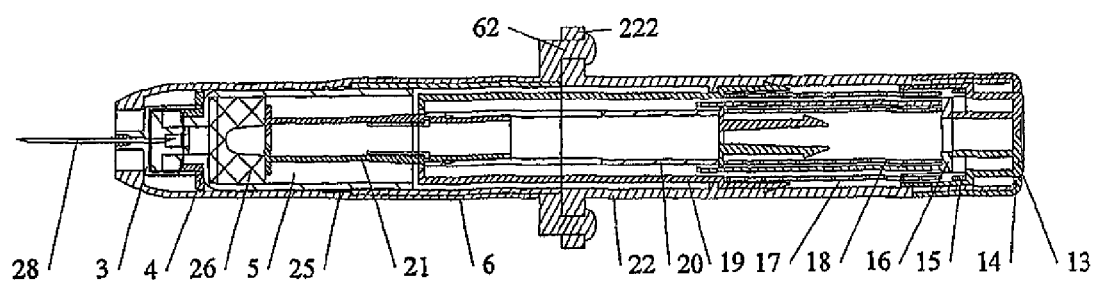
FIG. 22 is a cross-section view of the second embodiment of the automatic syringe for instant liquid-powder drug mixing and the embodiment of the automatic syringe for liquid drug after the drug injection operation is completed.

The injection operation in this embodiment is identical to embodiment 1 and will not be repeated. FIG. 21 and FIG. 22 show the states of the syringe during the needle feeding and after the injection are completed respectively.

3. The embodiment of the automatic syringe for liquid drug.

As shown in FIGS. 7-14, 16, and 20-22, the automatic syringe for liquid drug comprises an injecting assembly and a shooting device having parts and structures identical to that of the second embodiment. The difference is that this embodiment does not have a drug mixing assembly.

Before use, the injecting assembly and the shooting device are not connected and kept separately, as shown in FIGS. 14 and 16.

When in use, first coaxially connect the rear end of the injecting assembly and the front end of the shooting device, and then slightly turn the locating axle 62 until it clicks into the locating slot 222 of the shooting device. At this time the injecting assembly and the shooting device are integrated into one part and are ready for injection operation, as shown in FIG. 20.

The injection operation is identical to embodiment 2 and will not be repeated here. FIG. 21 and FIG. 22 show the state of needle feeding and after injection respectively.

The liquid drug automatic syringe according to the present invention does not require the drag mixing operation so the drug mixing assembly is omitted. Also there is no need for alternatively connecting the drug mixing assembly and the shooting device to the injecting assembly. And fixed connection type can be applied for the injecting assembly and the shooting device, for example, by screwing the rear end of the injecting outer sleeve 6 to the threaded front end of the shooting outer sleeve 22 or by tight connection, or the rear end of the injecting outer sleeve 6 and the shooting outer sleeve 22 can be fixed together. The water drug automatic syringe omits the step of joining the injecting assembly to the shooting device and directly goes to the step of the injection operation. Thus the connection structure between the injecting assembly and the shooting device is simplified.

Exemplary embodiments of the present invention have been disclosed herein and, it will be understood by those of ordinary skill in the art that various changes in form and details may be made without departing from the spirit and scope of the present invention as set forth in the following claims.

INDUSTRIAL APPLICABILITY

The automatic syringe for instant liquid-powder drug mixing and for liquid drug overcome the shortcomings of the existing syringe for medical use and the range of application is enlarged. Comparing with prior art, the automatic syringe of the present invention has at least the following advantages:

1. The menstruum, the solute and the syringe form a whole part of the automatic syringe for instant liquid-powder drug mixing of the present invention to simplify the drug-mixing and the drug-adding procedure, and the automatic syringe for liquid drug of the present invention integrates the liquid drug and the syringe to omit the drug adding procedure before injection. Both of them will shorten the preparation time before injection to improve work efficiency.

2. Similarly, the drug mixing and the drug adding procedure of the automatic syringe for instant liquid-powder drug mixing is completely performed inside the syringe, and the liquid drug automatic syringe does not has the drug mixing and the drug adding procedure at all, effectively avoiding the possible contamination during the drug mixing and drug adding procedure. The automatic syringes of the present invention are also suitable for use at non-medical facilities such as outside or battlefield.

3. The unique resilient pushing rod structure of the automatic syringe for instant liquid-powder drug mixing and the automatic syringe for liquid drug of the present invention makes the syringes have the function of automatic needle feeding and automatic injection, which has significant meaning for emergent rescue and battlefield self-rescue.

4. The automatic syringe for instant liquid-powder drug mixing and the automatic syringe for liquid drug of the present invention is not only easy to use, but also easy to carry.

5. The structure, applicability ad the cost effectiveness of the present invention meets the requirements of the development of the industry and the disclosed structure is new.

6. The structure of the syringe of the present invention is technically more advantageous to the existing syringes. The unique structure and function of the present invention is beyond compare to the existing syringes. Therefore the present invention is inventive.

7. As experienced in researching, designing and manufacturing of medical equipment, the applicant of the invention is very familiar with the defects of the syringes for medical use and the present invention is proposed in view of such defects to achieve the expected objects and functions. Therefore the present invention has industrial applicability.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. An automatic syringe for instant liquid-powder drug mixing characterized in that the syringe comprises a injecting assembly, a drug mixing assembly and a shooting device; wherein:

the injecting assembly includes a tubular injecting outer sleeve, in which a blocking ampoule is slidably socketed; the blocking ampoule contains the powder drug and has an open bottom end; a piston is provided inside the blocking ampoule; a needle having two piercing ends is coaxially connected to the mouth of the blocking ampoule through a hub; the needle is located to the front end of the injecting outer sleeve and the bottom of the blocking ampoule is located to the rear end of the injecting outer sleeve;

the drug-mixing assembly includes a tubular drug-mixing outer sleeve; the front end of the drug-mixing outer sleeve is closed having a hole in the centre; a menstruum bottle pre-charged with pressure is slidably socketed in the drug-mixing outer sleeve; a drug-mixing needle having two piercing ends is coaxially connected with the mouth of the menstruum bottle through a drug-mixing needle bracket; the drug-mixing needle is positioned to the front end of the drug-mixing outer sleeve and the bottom of the menstruum bottle is positioned to the rear end of the drug-mixing outer sleeve;

the shooting device includes a tubular shooting outer sleeve and a spring pushing rod mechanism slidably socketed in the shooting outer sleeve;

the rear end of the injecting assembly is alternatively connected with the front end of the drug-mixing assembly and the front end of the shooting device respectively through a rotary joining mechanism;

when the injecting assembly is coaxially connected to the drug-mixing assembly, the drug-mixing needle aims at the piston provided on the bottom of the injecting assembly;

when the injecting assembly is coaxially connected to the shooting device, the front end of the resilient pushing rod rests against the blocking ampoule and the piston.

2. The syringe according to claim 1, characterized in that the inner diameter of the injecting outer sleeve enlarges three times along the axis direction of the injecting outer sleeve from its front end to its rear end so as to form three annular steps on the inner wall of the injecting outer sleeve; in which the first annular step is positioned in the front portion of the inner wall of the injecting outer sleeve; the second annular step and the third annular step are positioned in the middle portion of the inner wall of injecting outer sleeve.

3. The syringe according to claim 2, characterized in that the hub is ring-shaped, the front end of the hub is a closed end and a hole is formed therein, the rear end of the hub is an open end and is slidably socketed with the mouth of the block ampoule; the hub is able to move forwardly along with the blocking ampoule until the front end of which is rested against the first annular step inside the injecting outer sleeve; the needle extends through the centre of the hub and is fixedly connected to the hub.

4. The syringe according to claim 3, characterized in that the front end of the hub is provided with a jacket for protecting the needle.

5. The syringe according to claim 2, characterized in that the injecting assembly further includes a cutting ring and a protective ring; wherein:

the cutting ring is a short tube made of thin steel sheet; the outer diameter of the cutting ring equals to or is slightly smaller than the inner diameter of the portion of the injecting outer sleeve between the second annular step and the third annular step; the length of the cutting ring in axis direction equals to the distance between the second annular step and the third annular step of the injecting outer sleeve, the rear end of the cutting ring gradually becomes thinner to form an annular cutting edge;

the annular-shaped protective ring is composed of two pieces of semicircular-shaped plates; the outer diameter of the protective ring is slightly smaller than the inner diameter of the cutting ring and is also slightly smaller than the inner diameter of the injecting outer sleeve in the portion before the second annular step; the hole in the centre of the protective ring allows the mouth of blocking ampoule to pass through; a tubular protrusion is formed around the hole extending to the front end; four connecting ribs are formed on the peripheral of the protective ring distributed in equal distances in radial direction of the protective ring; the total length of the outer diameter of the protective ring plus the lengths of any two opposite connecting ribs is slightly less than the length of the inner diameter of the portion of the injecting outer sleeve from the third annular step to the rear end to the injecting outer sleeve;

the cutting ring is rested against the second annular step inside the injecting outer sleeve, the tubular protrusion of the protective ring is rested against the neck of the blocking ampoule; the rear end of the protective ring is rested against the shoulder of the ampoule; the connecting ribs are forwardly rested against the third annular step in the injecting outer sleeve, and the cutting edge of the cutting ring barely touches the connecting ribs formed on the peripheral of the protective ring.

6. The syringe according to claim 1, characterized in that the opening front end of the injecting outer sleeve is provided with a protective cap.

7. The syringe according to claim 1, characterized in that the drug-mixing assembly further includes a bottle seat, a locking ring, a handle and a returning ring; wherein:
the front end of the bottle seat tightly receives the bottom of the menstruum bottle and rear end of the bottle seat is tightly connected to the handle;
the locking ring is tightly socketed or screwed on the rear end of the drug-mixing outer sleeve to restrict the position of the menstruum bottle to the inside the drug-mixing outer sleeve; the handle extends through the locking ring;
the menstruum bottle is in the returning ring; the front end and the rear end of the returning ring are rested against the inside of the front end of the drug-mixing outer sleeve and the front end of the bottle seat respectively.

8. The syringe according to claim 1, characterized in that the drug-mixing needle bracket has an annular shape; a hole is provided in the centre of the closed front end of the drug-mixing needle bracket to allow the drug-mixing needle to pass through the drug-mixing needle bracket and to be fixed on the needle bracket; the mouth of the menstruum bottle is slidably socketed in the open rear end of the needle bracket; claws are provided on the inner wall of the needle bracket to engaged with the rear edge of the mouth of the menstruum bottle.

9. The syringe according to claim 1, characterized in that the spring pushing rod mechanism includes a pushing rod for needle feeding, a pushing rod spring for needle feeding, a positioning ring, a pushing rod for injection, an extendable rod, a shooting cap, a shooting cap spring and a fastening ring; wherein:
the pushing rod for needle feeding, the positioning ring, the pushing rod for injection and the extendable rod have tubular shapes and are in turn slidably socketed with each other;
the diameter of the rear portion of the pushing rod is enlarged to form a step; a plurality of arrow-shaped pawls are formed on the rear end of the pushing rod to engage with the rear end of the shooting outer sleeve; protrusions for restricting the position are formed on the inner wall of the shooting outer sleeve to engage with the step form on the rear portion of the needle feeding pushing rod;
a positioning ring end face having a diameter larger than that of the positioning ring is formed on the rear end of the position ring; a hole is formed in the centre area of the end face of the positioning ring and two protrusions are formed on the two sides of the positioning ring end face respectively;
a slot is formed in one side of the pushing rod along its axis direction; arrow-shaped pawls are formed on the rear end of the pushing rod and extend through the centre hole of the positioning ring end face to engage with the rear end of the positioning ring end face;
a resilient buckle protruding outwardly and a protrusion are formed on the middle portion of the extendable rod; an end face of the extendable rod having a diameter larger than the extendable rod is formed on the front end of the extendable rod; the resilient buckle and the protrusion slidably engage with the slot of the pushing rod; the protrusion is rested against the rear end of the slot and the end face of the extendable rod is positioned outside the front end of the pushing rod;
a shooting cap has a double ring structure; the outer ring of the shooting cap has notches formed at the two sides corresponding to the protrusions of the positioning ring end face; the rear portion of the shooting cap has a smaller diameter to form a step and the rear end of the shooting cap is closed; the shooting cap is slidably socketed in the shooting outer sleeve; the positioning ring end face is received in the front end of the outer ring of the shooting cap which is rested against the pawls formed on the rear end of the pushing rod;
the rear end of the shooting outer sleeve is tightly socketed in the fastening ring to restrict the front portion of the shooting cap inside the shooting outer sleeve; the rear portion of the shooting cap extends through the ring hole;
the pushing rod spring for needle feeding is covered on the positioning rig and is positioned between the step formed inside the pushing rod and the positioning ring end face;
the pushing rod spring for injection is covered on the rear portion of the pushing rod and is positioned between the shoulder of the pushing rod on the rear end of the pushing rod and the positioning ring end face;
the shooting cap spring is positioned between the step formed inside the outer ring of the shooting cap and the positioning ring end face.

10. The syringe according to claim 1, characterized in that the movable joining mechanism further includes a centre rotary axle, two axle sleeves for the injecting assembly fixed to one side of the injecting outer sleeve, two axle sleeves for the drug-mixing assembly fixed to one side of the drug-mixing outer sleeve and two axle sleeves for the shooting device fixed to the side of the shooting outer sleeve; axle sleeves have open ends and are socketly connected to the centre rotary axle.

11. The syringe according to claim 10, characterized in that the movable joining mechanism further includes a locating axle fixed to rear end of the injecting outer sleeve opposite to the axle sleeves, a locating slot for the drug-mixing assembly fixed to the corresponding side of the front end of the drug-mixing outer sleeve, and a locating slot for the shooting device fixed to the corresponding side of the front end of the shooting outer sleeve; when the injecting assembly is coaxially connected to the drug-mixing assembly and the shooting device alternatively, the locating axle engages into the locating slot for the drug-mixing assembly and the locating slot for the shooting device alternatively.

12. The syringe according to claim 1, characterized in that the movable joining mechanism further includes two locating axles symmetrically formed on the peripheral of the rear end of the injecting outer sleeve, two locating slots for the drug-mixing assembly symmetrically formed on the peripheral of the front end of the drug-mixing outer sleeve and two locating slots for the shooting device symmetrically formed on the peripheral of the front end of the shooting outer sleeve; the locating axles alternatively engage with the locating slots for the drug-mixing assembly and the locating slots for the shooting device.

13. The syringe according to claim 1, characterized in that the rear end of the injecting outer sleeve is coaxially screwed to or tightly connected to the front end of the shooting outer sleeve.

14. The syringe according to claim 1, characterized in that the rear end of the injecting outer sleeve is fixedly connected to the front end of the shooting outer sleeve to integrate into a whole part.

15. The syringe according to claim 1, characterized in that locating axles are symmetrically formed on the peripheral of the rear end of the injecting outer sleeve, and locating slots for the shooting device are symmetrically formed on the peripheral of the front end of the shooting outer sleeve; the locating axles engages into the location slots for the shooting device.

* * * * *